(12) United States Patent
Biehl

(10) Patent No.: US 6,460,397 B1
(45) Date of Patent: Oct. 8, 2002

(54) METHOD AND DEVICE FOR DETERMINING THE SURFACE FRICTION COEFFICIENT IN BODIES

(75) Inventor: Margit Biehl, St. Wendel (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/554,055
(22) PCT Filed: Jan. 13, 1999
(86) PCT No.: PCT/DE99/00041
  § 371 (c)(1),
  (2), (4) Date: May 10, 2000
(87) PCT Pub. No.: WO99/39185
  PCT Pub. Date: Aug. 5, 1999

(30) Foreign Application Priority Data

Jan. 28, 1998 (DE) .......................... 198 03 219

(51) Int. Cl.⁷ .................... G01N 19/02; A61M 25/01
(52) U.S. Cl. ............................................. 73/9
(58) Field of Search .......................... 73/9, 10

(56) References Cited

U.S. PATENT DOCUMENTS

| 4,133,200 | * | 1/1979 | Cray | 73/10 |
| 5,403,295 | * | 4/1995 | Byrne | 604/265 |
| 5,776,771 | * | 7/1998 | Merkel et al. | 428/447 |

FOREIGN PATENT DOCUMENTS

| DE | 19533736 | * | 3/1997 | G01M/3/36 |
| EP | 491234 A2 | * | 6/1992 | 73/9 |
| GB | 2205960 A | * | 12/1988 | 73/9 |

* cited by examiner

Primary Examiner—Thomas P. Noland
(74) Attorney, Agent, or Firm—Breiner & Breiner, L.L.C.

(57) ABSTRACT

The present invention relates to a process and device for determining the surface friction coefficients of bodies, in particular of catheters. In the invented process, the to-be-examined catheter (1) is pulled with a defined velocity through a gel-like viscoelastic substance (2) and the frictional force required therefor is measured. A defined pressure is applied to this viscoelastic substance in such a manner that a defined surface normal force acts on the catheter surface. By applying a given, defined pressure on the substance, the surface pressure on each area element of the catheter surface is precisely given and can be held constant. By holding the area to which pressure is applied constant, the entire acting normal force can also be held constant and the friction coefficient can be determined for any catheter diameter and for any catheter consistency. Determination of the friction coefficient is reproducible and only depends on the surface friction.

11 Claims, 3 Drawing Sheets

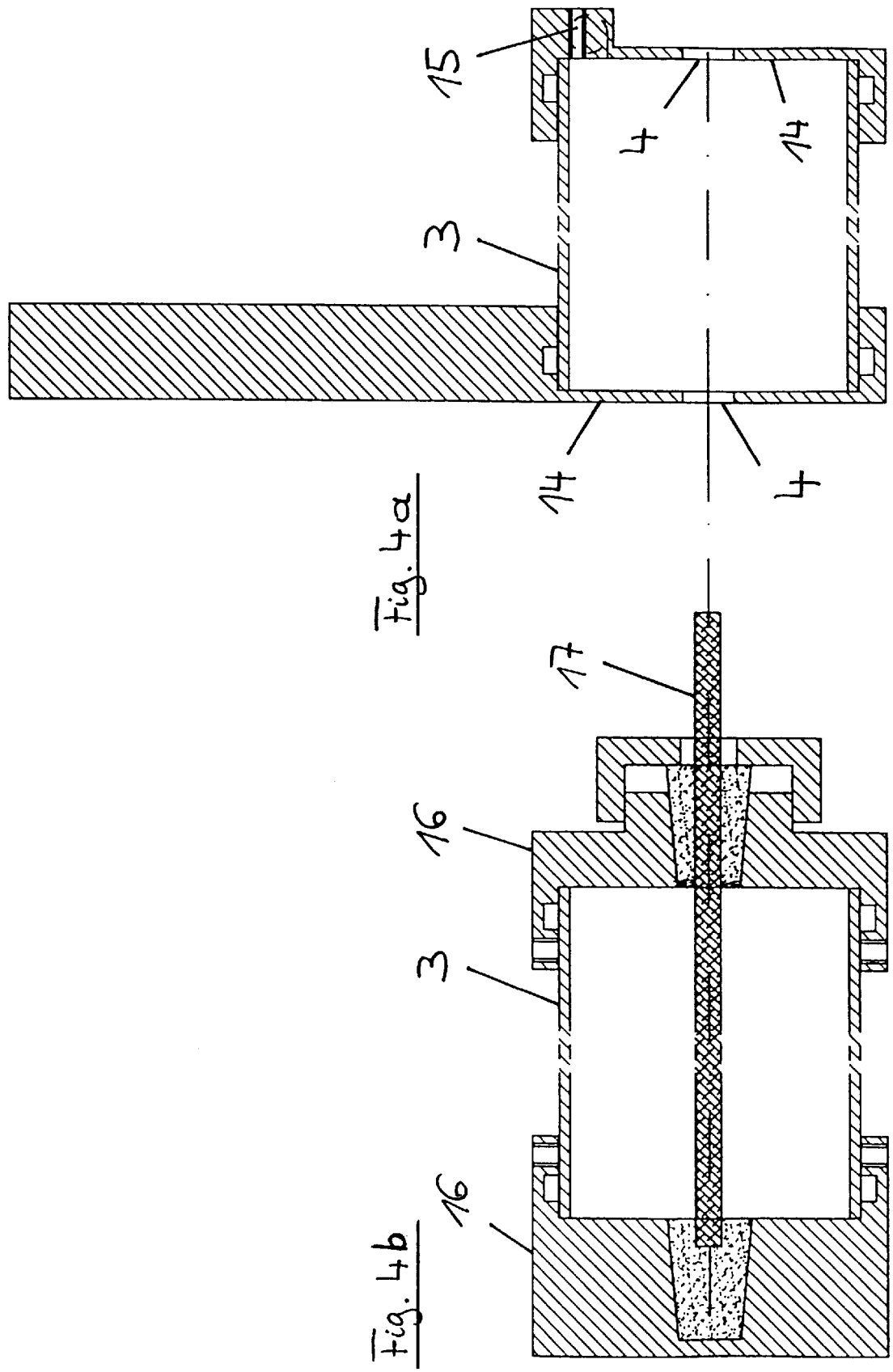

METHOD AND DEVICE FOR DETERMINING THE SURFACE FRICTION COEFFICIENT IN BODIES

FIELD OF INVENTION

The present invention relates to a process and a device for determining the surface friction coefficients of bodies, in particular of catheters.

BACKGROUND OF THE INVENTION

Medical catheters are subject to various surface treatments to, i.a., reduce the surface friction of the catheter in relation to the surrounding tissue in order to permit easier and painless insertion of the catheter, for instance into bloodstream in the case of heart catheters or into the urethra in the case of urinary catheters and to prevent possible injury to the tissue.

Catheters are often made of various, soft polymer materials, such as for example silicon rubber or polyurethane, which partially undergo different surface treatment. The purpose of this surface treatment is to smoothen and to hydrophilize in order to minimize surface friction as well as to reduce adhesion of proteins (bacteria). Strong hydrophilization of the surface decreases reciprocal energy in aqueous solutions and in that way the adhesion factor of frictional force.

Coats of different hydrogels, which feel slippery after submersion in water, have proven to be especially low-frictional. However, hitherto there is no standardized method of quantifying this "slipperiness" in the form of a surface friction coefficient so that presently it is not possible to quantitatively evaluate a reduction in friction due to a specific method of treating the surface.

Various attempts at measuring surface friction coefficients are already known in the state of the art. However, the measurement results determined with these known methods are not only dependent on the surface friction but also on the configuration and the consistency of the respective measured catheter and, therefore, cannot be compared with each other.

For example, many in vivo field tests were conducted for urinary catheters to determine the surface friction in the urethra of rabbits as well as humans (see Nickel, J. C. et al., "In Vivo Coefficient of Kinetic Friction: Study of Urinary Catheter Biocompatability", Urology XXIX (5), pp. 501–503 (1987); Khoury, A. E. et al., "Determination of the Coefficient of Kinetic Friction of Urinary Catheter Materials", The Journal of Urology 145, pp. 610–612 (1991); Tomita, N. et al., "Biomaterials Lubricated for Minimum Frictional Resistance", Journal of Applied Biomaterials 5, pp. 175–181 (1994)).

These tests are very realistic, but are unsuitable as a standard test method for catheter coatings, because particularly the muscle tone of the urethra of the individuals participating in biological tests differ. Consequently, no defined surface pressure can be applied to the catheter surface. As a result, the measured friction coefficients of a certain catheter on various individuals differ greatly.

Various attempts are also known of laboratory test systems. Two reports describe a test system in which two severed sections of the to-be-tested catheter are attached to a glass plate and are then loaded with a plane block of a defined weight coated with either collagen gel or hydrogel. A friction coefficient is determined by measuring the force needed to pull the block over the catheter (see Graiver, D. et al., "Surface Morphology and Friction Coefficient of Various Types of Foley Catheters", Biomaterials 14(6), pp. 465–469 (1993)) or by measuring the minimal oblique angle of the glass plate that is required to generate a slide movement of the block (see Nagaoka, S. et al., "Low-friction Hydrophilic Surface for Medical Devices", Biomaterials 11, pp. 419–424 (1990)). Contrary to real systems, counterform active area pairing occurs in these test systems, i.e. no full surface contact between the catheter and the block. Furthermore, surface pressure cannot be defined, because the contact surface varies depending on the softness and configuration of the tested catheter despite an unchanged weight load. Therefore, a normed friction coefficient cannot be determined with this method.

In two other methods (cf. Uyama, Y. et al., "Low-frictional Catheter Materials by Photo-Induced Graft Polymerization", Biomaterials 12, pp. 71–75 (1991)), the catheter is pulled through a bent PVC tube and the force required therefor is measured or a silicon rubber disc loaded at a defined weight is pulled over the catheter.

In both cases, there is largely conform active surface pairing, i.e. the areas of the catheter and the PVC tube respectively the silicon rubber disc are in surface contact. In the first instance, however, the normal force on the catheter cannot be defined and the size of the contact surface also varies, because the catheter deforms when pulled through the rigid tube. In the second case, the normal force varies over the contact surface and the contact surface itself also. Thus, the surface pressure cannot be precisely determined for different sizes of catheters. In both methods, an unsuited material is selected in addition for the counter body, because neither PVC nor silicon rubber is hydrophilic. Therefore, there is no similarity to real conditions when using catheters in the human or animal body.

Another attempt at determining the surface friction coefficients is known from MARMIERI, G. et al., "Evaluation of Slipperiness of Catheter Surfaces", Journal of Biomedical Materials Research (Applied Biomaterials) 33, pp. 29–33 (1996). In the test method presented there, the catheter is pulled through a block of hardened agar. The time required to pull a piece of catheter out of the agar by means of a defined load of weight is set as the measure of the slipperiness of the catheter.

However, no defined surface pressure on the catheter can be given with this test system. Therefore, its does not represent a standardized test method.

Thus, none of the processes or devices known from the state of the art permit standardized determination of the surface friction coefficient of catheters. The known processes yield measuring results that are not only dependent on the surface friction but also on the configuration and the consistency of the respectively measured catheter.

OBJECTS AND SUMMARY OF THE INVENTION

Therefore, the object of the present invention is to provide a standardized process and a device for determining the surface friction coefficients of bodies, in particular of catheters, whose measuring results are reproducible and only dependent on the surface friction and are independent of the configuration and the consistency of the material of the body itself.

This object is achieved with a process and a device according to claims 1 and 9. Advantageous embodiments are the subject matter of the subclaims.

In the invented process, the to-be-examined body, for example a catheter, is pulled with a defined velocity through a gel-like, soft, viscoelastic substance and the friction force required therefor is measured. In this process, a defined pressure is applied to this viscoelastic substance, the defined pressure spreading in the entire substance due to the viscoelastic material properties. As the catheter is enclosed in the substance for a specific length l( reciprocal action length), this pressure acts particularly also on the surface of the catheter. Thus a defined surface normal force is applied to the catheter surface. In this case, the entire charged area of the catheter is $A=l*\pi*d$, with d standing for the diameter of the catheter.

When measuring catheters of different diameters d, the invented process permits holding the entire area A constant by adapting the reciprocal action length l, on which the catheter comes into contact with the viscoelastic substance, conversely proportional to the diameter of the catheter: $l=A/(\pi*d)$. This can be achieved by adapting the size of the viscoelastic substance and the size of the container to receive this substance especially to each catheter diameter.

Measuring the force required to pull the catheter through the viscoelastic substance permits, with a given, known normal force, determining the surface friction coefficient of the catheter.

Of course, alternatively the viscoelastic substance can also be moved relative to a stationary catheter at a defined velocity.

The surface pressure on every surface element of the catheter surface can be exactly defined and kept constant by applying a presettable, defined pressure to the substance. Holding the surface to which pressure is applied constant permits keeping the entire acting normal force constant for every catheter diameter and for every catheter consistency. Thus, for every catheter configuration and consistency, a defined normal force exerted on a defined area of the catheter surface and the friction force can be measured. The ratio between the measured friction force and the preset normal force yields the friction coefficient. Determination of this friction coefficient is reproducible and depends only on the surface friction. Therefore, the invented process and the device therefor permit quantitative evaluation of the reduction in friction by using various methods of treating the surface of catheters.

The application of a preset, defined pressure to the substance is preferably realized by applying a defined surface pressure to a free surface of the substance. Thus, for instance, a surface pressure of approx. $10^4$ Pa can be applied to the free surface with the aid of a water column or by means of pumping in air or water into the container with the substance.

For a useful method of determining the surface friction coefficient of catheters, the given measurement conditions should be selected as close to real conditions as possible. Therefore, it seems useful to select a physiological saline solution with a temperature of 37° C. as the ambient medium for measuring.

The viscoelastic substance should like biological tissue be as hydrophilic as possible and be reproducible in its mechanical and chemical properties and be producible temporally stable. Hydrophilic, synthetic gel-like materials, so-called hydrogels, are therefore more suited as viscoelastic materials for this purpose than gels of natural origin.

In the following the present invention is made more apparent using preferred embodiments with reference to the drawings. They show in:

BRIEF DESCRIPTION OF THE DRAWINGS

FIG. 4a an example of a container according to the invented device;

FIG. 4b an example of an arrangement for filling the container according to FIG. 4a with a viscoelastic substance.

DETAILED DESCRIPTION OF PRESENTLY PREFERRED EMBODIMENTS

Figure 1:
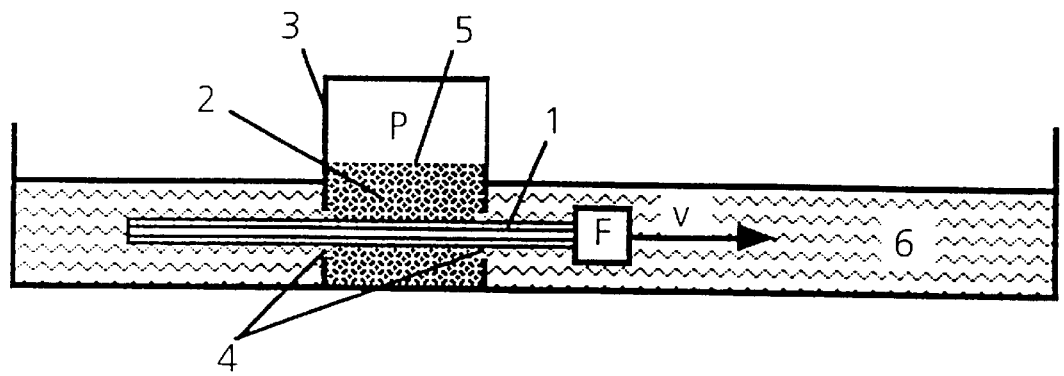
FIG. 1 a diagram of the measuring principle of the present invention.

FIG. 1 shows again the invented principle of the present process using a preferred embodiment. A to-be-examined catheter (1) is pulled with a defined velocity v through a gel-like soft, viscoelastic substance (2), and the friction force F required therefor is measured. The substance (2) fills the interior of a rigid container (3) in such a manner that it snuggles against the walls and floor of the container. This substance has a cylindrical lumen running through its center. The diameter of this lumen largely corresponds to the diameter of the catheter. The walls of the container, too, are provided with boreholes (4), the diameter of which is a little larger than that of the catheter, at both ends at the points of entry of the catheter so that the catheter does not rub against the wall of the container when pulled through the substance. A defined surface pressure P is applied to the free surface (5) of the viscoelastic substance spreading, after a period of relaxation, in the entire substance due to its viscoelastic properties. This pressure acts particularly on the surface of the catheter because the wall of the lumen running through the substance snuggles closely to the catheter wall due to its viscoelastic properties. Therefore, a surface normal force defined by the surface pressure P is applied to the catheter surface. The entire measurement can be conducted in a tub with an ambient medium (6) comprising a physiological saline solution at 37° C. comparable to the real conditions in human body. The surface pressure for urethra catheters range, for example, between approximately 4 cm $H_2O$ and 80 cm $H_2O$. A constant velocity v of 10 cm per minute, for example, can be selected for the relative movement between the catheter and the viscoelastic substance. However, the given values are, of course, only examples: depending on the demands, other velocities and a different surface pressure, can of course, be used.

For measuring catheters, preferably hydrogels are employed as the material for the viscoelastic substance. Hydrogels containing phosphoryl choline, a molecule that is also present in biomembranes, are advantageous. Furthermore, a hydrogel material (Hampshire's Hypol PreMA G 60) has advantages, because it is easy to work with. This is a polyurethane hydrogel prepolymer that cross links to form a polymer after a few seconds upon mixing with water yielding a firm, hydrophilic sponge rubber. A clear, hydrophilic gel can also be produced by stirring the prepolymer with water mixed with a large amount of acetone. In this case, the cross linking time increases to about half an hour permitting readily pouring this material into molds during this time. After cross linkage, the material has a firm, gel-like consistency with an abrasion-resistant, good wetting surface. After submersion in distilled water, it easily comes loose from glass surfaces in such a manner that a smooth surface can be poured with it. In particular, a mixture of one part prepolymer to eight parts acetone and two parts distilled water proved to yield a gel consistency quite similar to that of firm muscle tissue.

Figure 2:
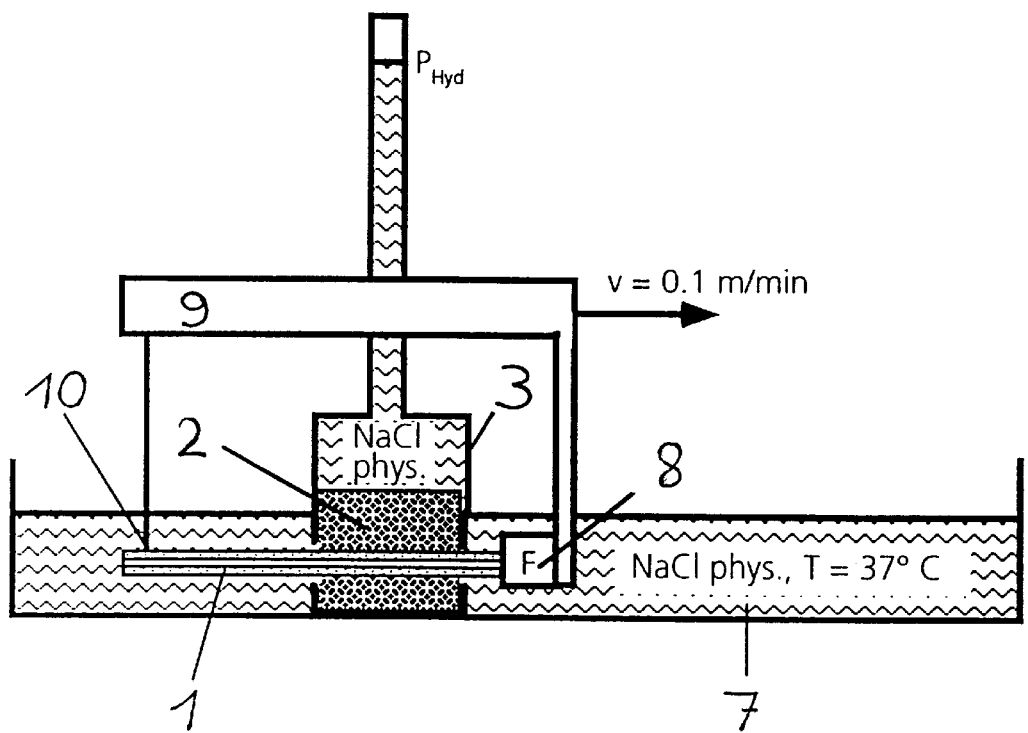
FIG. 2 a diagram of a preferred embodiment of a device of the present invention.

FIG. 2 shows an arrangement according to one of the preferred embodiments of the present invention. Herein the relative movement between a catheter (1) and the friction body in the form of a hydrogel (2) is achieved by the friction body being in a stationary defined position and the catheter (1) being pulled through the gel lumen with the aid of a mobile slide (9) at a defined velocity v. The tensile force, which after subtraction of the offset of the catheter clamp (10) corresponds to the surface friction, required therefor is measured with the aid of a force sensor (8) attached at the end of the catheter. In another preferred embodiment, shown in FIG. 3, catheter (1) is clamped tightly in a stationary frame (11) in such a manner that its position remains fixed. The container (3) with the hydrogel (2) is then pulled with the aid of a moveable slide (9) over the catheter (1) at a defined velocity v. In this case, too, the force measured with the force sensor (8) attached at one end of the catheter corresponds to the surface friction if the clamping force held constant via the guide pulley (12) by means of the weight (13) is subtracted.

Figure 3:
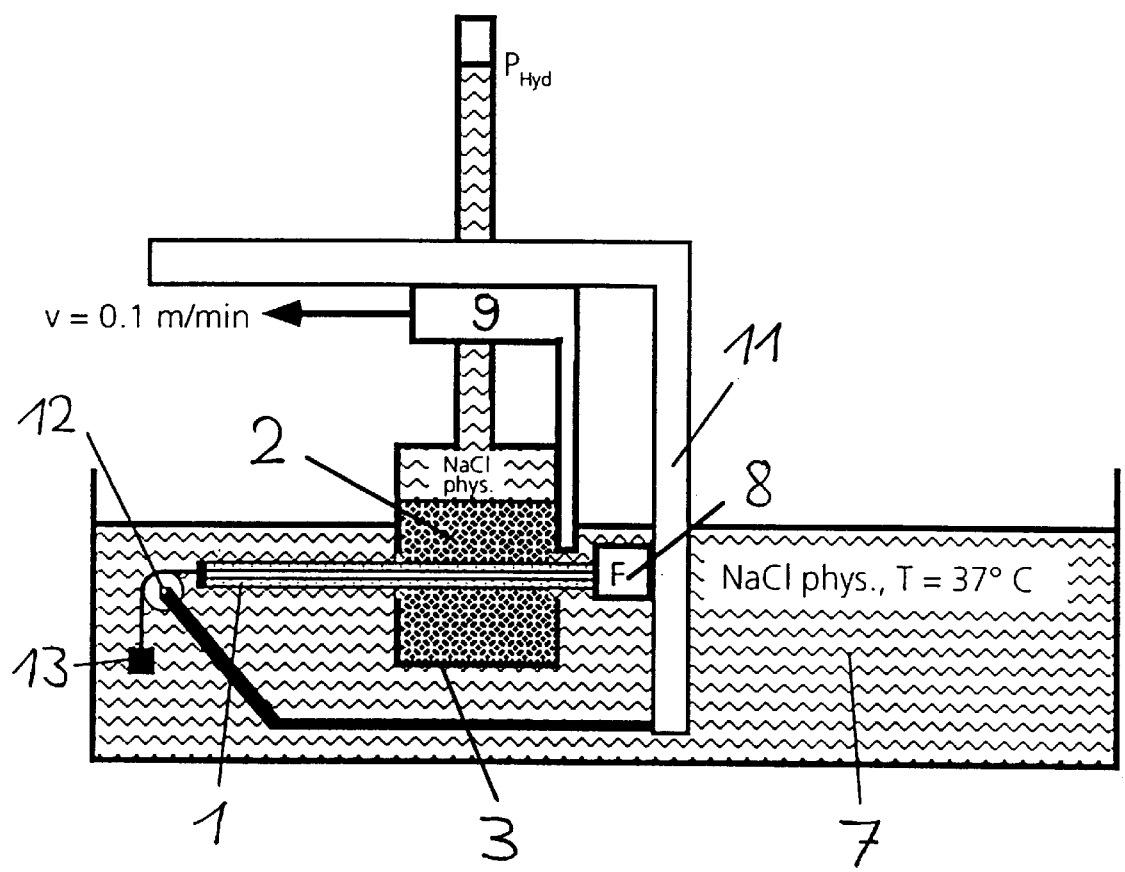
FIG. 3 a diagram of another preferred embodiment of a device of the present invention.

In both embodiments shown in FIGS. 2 and 3, the surface pressure can be given in a defined manner, for example, by the hydrostatic pressure of a water column (here: physiological saline solution). A glass burette suspended at a corresponding height (well 1 m over the catheter) from a meter rule, for instance, can serve as a container for the water column. The bottom end of the burette is connected to the hydrogel container via a flexible hose connection.

A piece of tube positioned horizontally in axial direction and closed at both ends by a sealing lid (14) with a central opening (4) respectively for passage of the catheter can serve as the container (3) for the hydrogel (as viscoelastic substance). An example of such a container is shown in FIG. 4a. The container length suited for the respective catheter size can then be obtained simply by inserting a tube shortened to the required length and filled with hydrogel. One of the lids is provided in addition with an opening (15) through which pressure can be applied to the interior of the container.

As preparation for measurement, the tube is transformed into a mold by closing suited lids (16) at both ends as shown in FIG. 4b. In order to obtain a required lumen in the hydrogel mass, a stainless steel or glass rod (17) is enclosed inside the hydrogel (not shown). The diameter of the stainless steel or glass rod (17) corresponds largely to the diameter of the to-be-examined catheter. The rod is removed following complete vulcanization of the hydrogel and a correspondingly dimensioned recess remains in the gel.

A length of the hydrogel container (3) of, for example, 150 mm for a catheter diameter of 2 mm yields a contact surface of 942 mm² due to which, with a hydrostatic pressure of, for instance $10^4$ Pa (approx. 1 m water column), the overall normal force of 9.42; N acts on the catheter surface. Assuming a catheter surface friction coefficient in the vicinity of $\mu$=0.1, one measures with the described measuring device a friction force of about 1N. For larger catheter diameters, one needs correspondingly shorter hydrogel containers in order to keep the contact surface constant. For example, a container with a length of 60 mm is used for a catheter with a diameter of 5 mm.

With the invented process and the device therefor, the same surface pressure can be applied to catheters of different diameters in such a manner that a direct comparison of the determined surface friction coefficient is possible independent of the configuration and consistency of the respective measured catheter.

The invented process and device therefor are, of course, also suited for determining the surface friction of other bodies as catheters. The preferred application relates to bodies that come into contact with biological tissue, i.e., are inserted into, for example, the bloodstream, urethra or the like.

What is claimed is:

1. A process for determining a surface friction coefficient of a body, comprising enclosing the body in a gel-like viscoelastic substance over a reciprocal action length, generating between said body and said substance a relative movement with constant velocity and measuring a force required therefor, wherein a presettable, defined pressure is applied to said substance at least during said relative movement; said reciprocal action length is selected in such a manner that a defined surface normal force acts via said substance on an area of said body preselectable by said reciprocal action length; and said surface friction coefficient is determined from the ratio of the measured force to the surface normal force.

2. The process according to claim 1, wherein said substance has a free surface to which a defined, given surface pressure is applied to generate said defined pressure.

3. The process according to claim 2, wherein pressure is applied to said free surface of said substance via gas or water pressure.

4. The process according to claim 1 or 2, wherein said body is a catheter.

5. The process according to claim 4, wherein with catheters of different diameters $d_i$, said reciprocal action length $l_i$ is selected for each said catheter in such a manner that on each said catheter pressure is applied to the same constant area $A=l_i*n*d_i$.

6. The process according to claim 1, wherein said body is pulled through said substance.

7. The process according to claim 1, wherein said substance is pulled over said body.

8. The process according to claim 1, wherein said substance is a hydrogel.

9. A device for determining a surface friction coefficient of a body, based on a ratio of measured force to a surface normal force, comprising a container containing a gel-like viscoelastic substance in which the body is enclosed over a reciprocal action length, a relative movement with constant velocity being generated between said body and said substance and a force required therefore measured, said container having an inlet opening and an outlet opening which permit pulling said body through said substance in order to generate the relative movement between said body and said substance and another opening for applying a presettable defined pressure to said substance at least during the relative movement.

10. The device according to claim 9, further comprising a slide for attaching said body with which said body can be moved relative to said container with constant velocity.

11. The device according to claim 9, further comprising a slide for attaching said container with which said container can be moved relative to said body with constant velocity.

* * * * *

UNITED STATES PATENT AND TRADEMARK OFFICE
CERTIFICATE OF CORRECTION

PATENT NO. : 6,460,397 B1
DATED : October 8, 2002
INVENTOR(S) : Margit Biehl

It is certified that error appears in the above-identified patent and that said Letters Patent is hereby corrected as shown below:

Title page,
Item [54], "METHOD AND DEVICE FOR DETERMINING THE SURFACE FRICTION COEFFICIENT IN BODIES" should read -- PROCESS AND DEVICE FOR DETERMINING THE SURFACE FRICTION COEFFICIENT IN BODIES --.

Column 1,
Line 1, "METHOD" should read -- PROCESS --.

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,460,397 B1
DATED         : October 8, 2002
INVENTOR(S)   : Margit Biehl It is certified that error appears in the above-identified patent and that said Letters Patent is hereby corrected as shown below:

Title page, Item [54] and Column 1, lines 1-3,
"METHOD AND DEVICE FOR DETERMINING THE SURFACE FRICTION COEFFICIENT IN BODIES" should read -- PROCESS AND DEVICE FOR DETERMINING THE SURFACE FRICTION COEFFICIENTS OF BODIES --.

Column 3,
Line 61, insert the heading -- BRIEF DESCRIPTION OF THE DRAWINGS --.
Line 65, delete the heading "BRIEF DESCRIPTION OF THE DRAWINGS".

Column 6,
Line 35, "$A=1_i*n*d_i$" should read -- $A=1_i*\pi*d_i$ --.

Signed and Sealed this

Twenty-sixth Day of August, 2003

JAMES E. ROGAN
*Director of the United States Patent and Trademark Office*